US010694957B2

(12) United States Patent
Martin et al.

(10) Patent No.: US 10,694,957 B2
(45) Date of Patent: Jun. 30, 2020

(54) SYSTEM AND METHOD FOR OBTAINING BODILY FUNCTION MEASUREMENTS USING A MOBILE DEVICE

(71) Applicant: QUALCOMM Incorporated, San Diego, CA (US)

(72) Inventors: Russel Allyn Martin, Menlo Park, CA (US); Leonid Sheynblat, Hillsborough, CA (US); Douglas Wayne Hoffman, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 16/137,425

(22) Filed: Sep. 20, 2018

(65) Prior Publication Data

US 2019/0021606 A1 Jan. 24, 2019

Related U.S. Application Data

(63) Continuation of application No. 14/278,062, filed on May 15, 2014, now Pat. No. 10,478,075.

(Continued)

(51) Int. Cl.
*A61B 5/00* (2006.01)
*A61B 5/021* (2006.01)
(Continued)

(52) U.S. Cl.
CPC .......... *A61B 5/021* (2013.01); *A61B 5/02028* (2013.01); *A61B 5/0261* (2013.01);
(Continued)

(58) Field of Classification Search
CPC ............ A61B 5/02125; A61B 5/02158; A61B 5/0031; A61B 5/02416; A61B 5/042;
(Continued)

(56) References Cited

U.S. PATENT DOCUMENTS 8,419,649 B2 4/2013 Banet et al.
10,052,035 B2 8/2018 Martin et al.
(Continued)

FOREIGN PATENT DOCUMENTS

CN 103228205 A 7/2013
EP 0638281 A1 2/1995
(Continued)

OTHER PUBLICATIONS

International Preliminary Report on Patentability—PCT/US2014/061122, The International Bureau of WIPO—Geneva, Switzerland, dated Mar. 22, 2016.
(Continued)

*Primary Examiner* — Elmer M Chao
(74) *Attorney, Agent, or Firm* — Kilpatrick Townsend & Stockton LLP

(57) ABSTRACT

Methods, systems, computer-readable media, and apparatuses for obtaining at least one bodily function measurement are presented. A mobile device includes an outer body sized to be portable for user, a processor contained within the outer body, and a plurality of sensors physically coupled to the outer body. The sensors are configured to obtain a first measurement indicative of blood volume and a second measurement indicative of heart electrical activity in response to a user action. A blood pressure measurement is determined based on the first measurement and the second measurement. The sensors also include electrodes where a portion of a user's body positioned between the electrodes completes a circuit and a measurement to provide at least one measure of impedance associated with the user's body. A hydration level measurement is determined based on the measure of impedance.

20 Claims, 10 Drawing Sheets

Related U.S. Application Data

(60) Provisional application No. 61/895,995, filed on Oct. 25, 2013.

(51) Int. Cl.
*A61B 5/026* (2006.01)
*A61B 5/0404* (2006.01)
*A61B 5/02* (2006.01)
*A61B 5/04* (2006.01)
*A61N 1/365* (2006.01)
*A61B 5/042* (2006.01)
*A61B 5/024* (2006.01)
*A61B 5/0215* (2006.01)

(52) U.S. Cl.
CPC ........ *A61B 5/0404* (2013.01); *A61B 5/04012* (2013.01); *A61B 5/681* (2013.01); *A61B 5/6824* (2013.01); *A61B 5/6898* (2013.01); *A61B 5/0031* (2013.01); *A61B 5/02125* (2013.01); *A61B 5/02158* (2013.01); *A61B 5/02416* (2013.01); *A61B 5/042* (2013.01); *A61N 1/36507* (2013.01); *A61N 1/36564* (2013.01); *A61N 1/36585* (2013.01)

(58) Field of Classification Search
CPC .............. A61B 5/0452; A61N 1/36564; A61N 1/36507; A61N 1/36585
See application file for complete search history.

(56) References Cited

U.S. PATENT DOCUMENTS

| | | | |
|---|---|---|---|
| 2005/0239493 A1* | 10/2005 | Batkin | A61B 5/0404 455/550.1 |
| 2007/0021677 A1* | 1/2007 | Markel | A61B 5/0006 600/509 |
| 2009/0073991 A1 | 3/2009 | Landrum et al. | |
| 2009/0105556 A1 | 4/2009 | Fricke et al. | |
| 2010/0049059 A1 | 2/2010 | Ha et al. | |
| 2010/0160793 A1 | 6/2010 | Lee et al. | |
| 2010/0160796 A1 | 6/2010 | Banet et al. | |
| 2010/0217099 A1 | 8/2010 | Leboeuf et al. | |
| 2011/0066010 A1 | 3/2011 | Moon et al. | |
| 2011/0245690 A1 | 10/2011 | Watson et al. | |
| 2012/0215275 A1 | 8/2012 | Wenzel et al. | |
| 2012/0245480 A1 | 9/2012 | Chong et al. | |
| 2013/0005303 A1* | 1/2013 | Song | A61B 5/02438 455/411 |
| 2013/0085356 A1 | 4/2013 | Schlottau et al. | |
| 2013/0263252 A1 | 10/2013 | Lien et al. | |
| 2015/0119654 A1 | 4/2015 | Martin et al. | |
| 2015/0119725 A1 | 4/2015 | Martin et al. | |

FOREIGN PATENT DOCUMENTS

| | | |
|---|---|---|
| EP | 1977688 A2 | 10/2008 |
| EP | 2644089 A1 | 10/2013 |
| JP | H0731594 A | 2/1995 |
| JP | H0795966 A | 4/1995 |
| JP | H07116141 A | 5/1995 |
| JP | 2001178692 A | 7/2001 |
| JP | 2001258860 A | 9/2001 |
| JP | 2002165768 A | 6/2002 |
| JP | 2005006824 A | 1/2005 |
| JP | 2006263354 A | 10/2006 |
| JP | 2007502675 A | 2/2007 |
| JP | 2007236917 A | 9/2007 |
| JP | 2008073461 A | 4/2008 |
| JP | 2010046494 A | 3/2010 |
| JP | 2011120917 A | 6/2011 |
| WO | 2010125705 A1 | 11/2010 |
| WO | 2012099535 A1 | 7/2012 |

OTHER PUBLICATIONS

International Preliminary Report on Patentability—PCT/US2014/062425, The International Bureau of WIPO—Geneva, Switzerland, dated May 6, 2016.
International Search Report and Written Opinion—PCT/US2014/061122—ISA/EPO—dated Dec. 19, 2014.
International Search Report and Written Opinion—PCT/US2014/062425—ISA/EPO—dated Jan. 23, 2015.
Kim Y., et al., "Cuffless and Non-invasive Estimation of a continuous blood pressure based on PTT", IEEE, 2010, pp. 4.
Labat M., et al., "Wearable Blood Pressure Monitoring System—Case Study of Multiplatform Applications for Medical Use," In Proceedings of the International Conference on Health Informatics, 2011, pp. 156-163.

* cited by examiner

Fricke's circuit
Two parallel electrical conductors:
  $R_{(ECW)}$: $H_2O$-Na
  $R_{(ICW)}$: $H_2O$-K
isolated by a cell membrane ($X_c$)

SYSTEM AND METHOD FOR OBTAINING BODILY FUNCTION MEASUREMENTS USING A MOBILE DEVICE

CROSS-REFERENCE TO RELATED APPLICATIONS

This application is a continuation of U.S. application Ser. No. 14/278,062, filed May 15, 2014, entitled "SYSTEM AND METHOD FOR OBTAINING BODILY FUNCTION MEASUREMENTS USING A MOBILE DEVICE," which claims priority to U.S. Provisional Application No. 61/895,995, filed Oct. 25, 2013, entitled "SYSTEM AND METHOD FOR OBTAINING BODILY FUNCTION MEASUREMENTS USING A MOBILE DEVICE" which is incorporated herein by reference.

BACKGROUND

Aspects of the disclosure relate to mobile devices, and more particularly, a system and method for obtaining at least one bodily function measurement of a user operating a mobile device.

It is often desirable for a user to be aware his/her bodily function measurements, which may provide physiological measures of stress, measures of hydration, and other measures of general health. Physiological measures of stress may be used to communicate to a user instructions to alter his/her behavior, e.g., taking a break, taking deep breaths, etc. Measures of hydration may be used by athletes or generally active individuals to ensure that they stay hydrated to maintain physical performance. Additionally, this information may be useful for individuals who work in hot or dry environments and must maintain proper hydration. Further, this information may be useful for elderly individuals whose sense of hydration is decreased and are more prone to becoming dehydrated. Thus, important bodily function measurements may include measurements of a user's blood pressure and/or hydration state.

A user's blood pressure may be measured using a pulse-measuring device. Typical pulse-measuring devices use either photoplethysmography (PPG) or electrocardiography (ECG) to measure a user's pulse. A user's systolic blood pressure or diastolic blood pressure may be determined using a combination of the PPG and ECG using a technique known as pulse transit time (PTT). The systolic blood pressure, along with other inputs such as pulse rate variability (PRV) and galvanic skin response (GSR) may be useful in determining the user's physiological measures of stress. However, existing mobile device solutions for obtaining PPG measurements and ECG measurements can only obtain measurements for one or the other. That is, existing mobile device solutions can only obtain a PPG measurement or an ECG measurement, but not both.

A user's hydration state may be determined by measuring a total body water amount using a bioelectric impedance analysis (BIA). BIA measurements are typically accurate and may fall within 200 ml of the actual value when performed properly. Typically, existing solutions to measure BIA require professional equipment in a clinical setting. Additionally, the few devices that exist to measure BIA outside of a clinical setting are not very mobile, e.g., they may not fit within a user's pocket or be integrated into another device that the user typically always has with them.

Accordingly, a need exists for a mobile solution to obtain both PPG and ECG measurements used for determining a user's blood pressure and to obtain a body water content measurement used for determining a user's hydration state.

BRIEF SUMMARY

Certain embodiments are described that for obtaining at least one bodily function measurement of a user operating a mobile device.

In some embodiments, a mobile device for obtaining at least one bodily function measurement comprises an outer body sized to be portable for a user, a processor contained within the outer body, and a plurality of sensors physically coupled to the outer body for obtaining data accessible by the processor. One or more sensors of the sensors is configured to obtain a first measurement indicative of blood volume in response to a user action. One or more of the sensors is configured to obtain a second measurement indicative of heart electrical activity in response to the user action. The processor is configured to facilitate generation of a blood pressure measurement based on the first measurement and the second measurement.

In some embodiments, the mobile device is configured to perform a primary function and a secondary function, and wherein the processor is configured to facilitate generation of the blood pressure measurement as the secondary function of the mobile device.

In some embodiments, the first measurement indicative of blood volume comprises a photoplethysmography (PPG) measurement.

In some embodiments, the second measurement indicative of heart electrical activity comprises an electrocardiography (ECG) measurement.

In some embodiments, the one or more of the sensors configured to obtain the first measurement comprises at least one light sensor, and wherein the mobile device further comprises at least one light source and the at least one light sensor measures reflected light from the light source reflected off of blood vessels within a user of the mobile device to obtain the first measurement.

In some embodiments, the one or more of the sensors configured to obtain the second measurement indicative of blood volume comprises at least a first electrode and a second electrode, and wherein a portion of a user of the mobile device's body completes a circuit between the first electrode and the second electrode.

In some embodiments, the mobile device is a watch.

In some embodiments, the mobile device is a smartphone device.

In some embodiments, method for obtaining at least one bodily function measurement via a mobile device comprises obtaining, via a plurality of sensors physically coupled to an outer body of the mobile device, a first measurement indicative of blood volume in response to a user action. The method further comprises obtaining, via the plurality of sensors, a second measurement indicative of heart electrical activity in response to the user action. The method also comprises facilitating, via a processor of the mobile device, generation of a blood pressure measurement based on the first measurement and the second measurement, wherein the processor is contained within the outer body of the mobile device, the outer body sized to be portable for the user.

In some embodiments, an apparatus for obtaining at least one bodily function measurement comprises means for obtaining, via a plurality of sensors physically coupled to an outer body of a mobile device, a first measurement indicative of blood volume in response to a user action. The method further comprises means for obtaining, via the plurality of sensors, a second measurement indicative of heart electrical activity in response to the user action. The method also comprises means for facilitating, via a processor of the mobile device, generation of a blood pressure measurement based on the first measurement and the second measurement, wherein the processor is contained within the outer body of the mobile device, the outer body sized to be portable for the user.

In some embodiments, one or more non-transitory computer-readable media storing computer-executable instructions for obtaining at least one bodily function measurement that, when executed, cause one or more computing devices included in a mobile device to obtain, via a plurality of sensors physically coupled to an outer body of the mobile device, a first measurement indicative of blood volume in response to a user action. The computer-executable instructions, when executed, further cause the one or more computing devices included in a device to obtain, via the plurality of sensors, a second measurement indicative of heart electrical activity in response to the user action. The computer-executable instructions, when executed, further cause the one or more computing devices included in a device to facilitate, via a processor of the mobile device, generation of a blood pressure measurement based on the first measurement and the second measurement, wherein the processor is contained within the outer body of the mobile device, the outer body sized to be portable for the user.

In some embodiments, a mobile device for obtaining at least one bodily function measurement comprises an outer body sized to be portable for a user, a processor contained within the outer body, and a plurality of sensors physically coupled to the outer body for obtaining data accessible by the processor. The plurality of sensors comprises electrodes and a portion of a user's body positioned between the electrodes completes a circuit and a measurement to provide at least one measure of impedance associated with the user's body in response to a user action. The processor is configured to facilitate generation of a hydration level measurement based on the measure of impedance.

In some embodiments, the mobile device is configured to perform a primary function and a secondary function, and wherein the processor is configured to facilitate generation of the hydration level measurement as the secondary function of the mobile device.

In some embodiments, at least one of the sensors is built into a multifunction surface, wherein the multifunction surface is configured to simultaneously obtain the impedance measurement and a user input.

In some embodiments, the multifunction surface comprises silver metal.

In some embodiments, the multifunction surface comprises Indium Tin Oxide (ITO).

In some embodiments, the mobile device is a watch.

In some embodiments, the mobile device is a smartphone device.

In some embodiments, a method for obtaining at least one bodily function measurement via a mobile device comprises obtaining, via a plurality of sensors comprising electrodes and physically coupled to an outer body of the mobile device, a measurement to provide at least one measure of impedance associated with a user's body in response to a user action, wherein a portion of the user's body positioned between the electrodes completes a circuit. The method also comprises facilitating, via a processor of the mobile device, generation of a hydration level measurement based on the measure of impedance, wherein the processor is contained within the outer body of the mobile device, the outer body sized to be portable for the user.

In some embodiments, an apparatus for obtaining at least one bodily function measurement via a mobile device comprises means for obtaining, via a plurality of sensors comprising electrodes and physically coupled to an outer body of the mobile device, a measurement to provide at least one measure of impedance associated with a user's body in response to a user action, wherein a portion of the user's body positioned between the electrodes completes a circuit. The apparatus further comprises means for facilitating, via a processor of the mobile device, generation of a hydration level measurement based on the measure of impedance, wherein the processor is contained within the outer body of the mobile device, the outer body sized to be portable for the user.

In some embodiments, one or more non-transitory computer-readable media storing computer-executable instructions for obtaining at least one bodily function measurement that, when executed, cause one or more computing devices included in a mobile device to obtain, via a plurality of sensors comprising electrodes and physically coupled to an outer body of the mobile device, a measurement to provide at least one measure of impedance associated with a user's body in response to a user action, wherein a portion of the user's body positioned between the electrodes completes a circuit. The computer-executable instructions, when executed, further cause the one or more computing devices included in a device to facilitate, via a processor of the mobile device, generation of a hydration level measurement based on the measure of impedance, wherein the processor is contained within the outer body of the mobile device, the outer body sized to be portable for the user.

BRIEF DESCRIPTION OF THE DRAWINGS

Aspects of the disclosure are illustrated by way of example. In the accompanying figures, like reference numbers indicate similar elements, and.

DETAILED DESCRIPTION

Several illustrative embodiments will now be described with respect to the accompanying drawings, which form a part hereof. While particular embodiments, in which one or more aspects of the disclosure may be implemented, are described below, other embodiments may be used and various modifications may be made without departing from the scope of the disclosure or the spirit of the appended claims.

Figure 1:
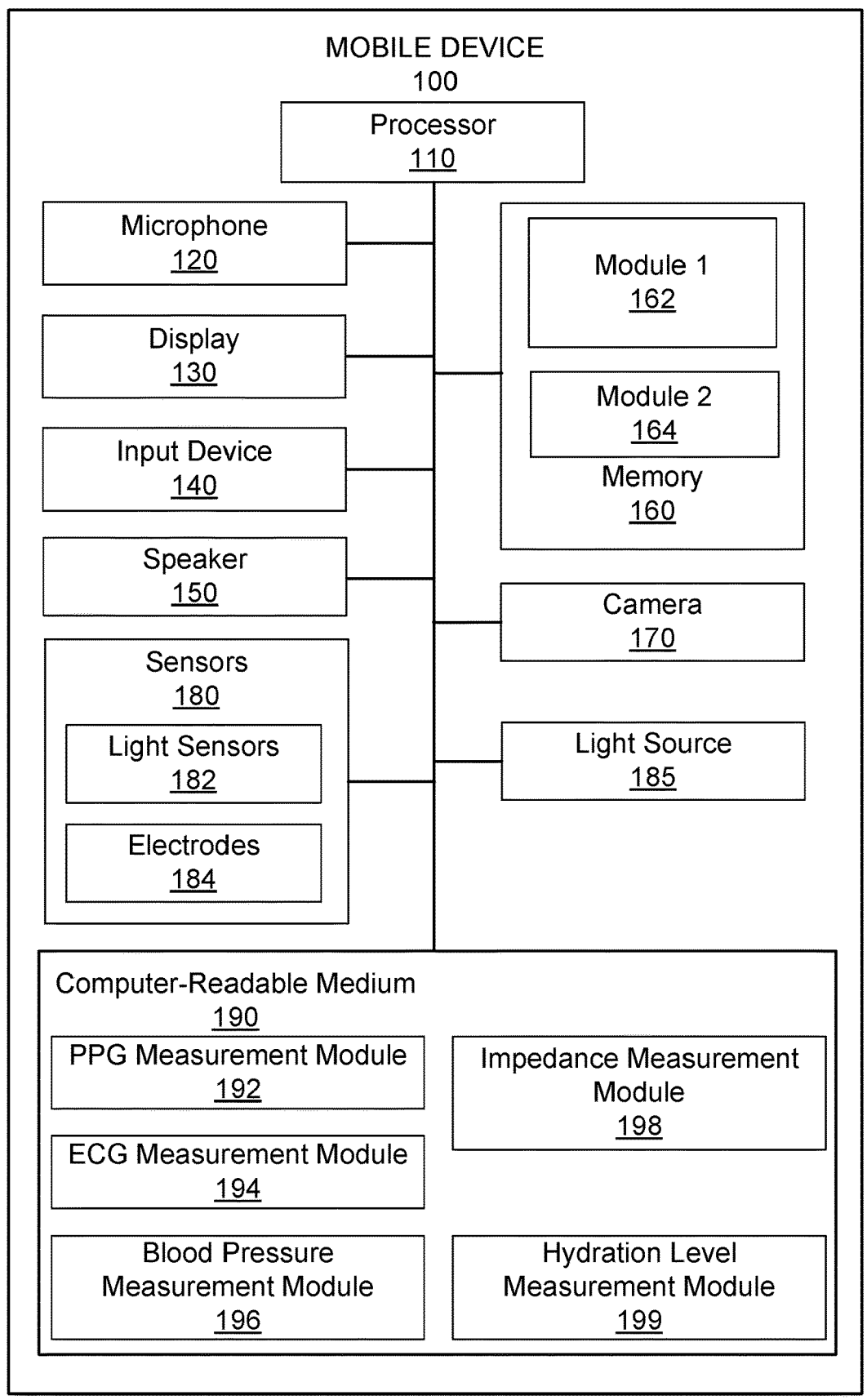
FIG. 1 illustrates a smartphone device configured to obtain PPG and ECG measurements of a user, according to some embodiments.

FIG. 1 illustrates a simplified block diagram of a mobile device 100 that may incorporate one or more embodiments. Mobile device 100 includes a processor 110, microphone 120, display 130, input device 140, speaker 150, memory 160, camera 170, sensors 180, light source 185, and computer-readable medium 190.

Processor 110 may be any general-purpose processor operable to carry out instructions on the mobile device 100. The processor 110 is coupled to other units of the mobile device 100 including microphone 120, display 130, input device 140, speaker 150, memory 160, camera 170, sensors 180, light source 185, and computer-readable medium 190.

Microphone 120 may be any an acoustic-to-electric transducer or sensor that converts sound into an electrical signal. The microphone 120 may provide functionality for a user of the mobile device 100 to record audio or issue voice commands for the mobile device 100.

Display 130 may be any device that displays information to a user. Examples may include an LCD screen, CRT monitor, or seven-segment display.

Input device 140 may be any device that accepts input from a user. Examples may include a keyboard, keypad, or mouse. In some embodiments, the microphone 120 may also function as an input device 140.

Speaker 150 may be any device that outputs sound to a user. Examples may include a built-in speaker or any other device that produces sound in response to an electrical audio signal and/or ultrasonic signal(s).

Memory 160 may be any magnetic, electronic, or optical memory. Memory 160 includes two memory modules, module 1 162 and module 2 164. It can be appreciated that memory 160 may include any number of memory modules. An example of memory 160 may be dynamic random access memory (DRAM).

Camera 170 is configured to capture one or more images via a lens located on the body of mobile device 100. The captured images may be still images or video images. The camera 170 may include a CMOS image sensor to capture the images. Various applications running on processor 110 may have access to camera 170 to capture images. It can be appreciated that camera 170 can continuously capture images without the images actually being stored within the mobile device 100. Captured images may also be referred to as image frames.

Sensors 180 may be a plurality of sensors configured to obtain data accessible by the processor. The sensors 180 may also be physically coupled to the outer body of the mobile device 100. The plurality of sensors 180 may include one or more light sensors 182 and/or one or more electrodes 184. The light sensors 182 may be configured to facilitate measurement of reflected light from the light source 185 (described below) reflected off of blood vessels within a user of the mobile device 100 to obtain the a PPG measurement indicative of the user's blood volume. A portion of a user of the mobile device's 100 body may complete a circuit between a first electrode and a second electrode, e.g., when the user touches both electrodes 184. The electrodes 184 may be configured to facilitate measurement of heart electrical activity of the user to obtain an ECG measurement. The electrodes 184 may also be configured to facilitate measurement of impedance of the user of the mobile device 100 to obtain a level measurement.

Light source 185 may be any source of light configured to emit light through a user's body. In some embodiments, the light source 185 may be a LED light source. The emitted light may be of a wavelength that can pass through parts of a user's body. For example, the light source 185 may emit LED light through a user's wrist. In some embodiments, the mobile device 100 may include multiple light sources 185. The light emitted from light source 185 may reflect off of blood vessels within the user's body and the reflected light may be measured by one or more light sensors 182 to obtain a PPG measurement, as described above. It can be appreciated that emitted light may be of different wavelengths depending on different wavelengths. For example, different wavelengths of light may be appropriate to improve the signal, reduce noise, deal with dark skin colors, measure the blood's oxygen content, or penetrate to different depths of the user's body.

Computer-readable medium 190 may be any magnetic, electronic, optical, or other computer-readable storage medium. Computer-readable storage medium 190 includes PPG measurement module 192, ECG measurement module 194, blood pressure measurement module 196, impedance measurement module 198, and hydration level measurement module 199.

PPG measurement module 192 is configured to, when executed by processor 110, obtain a photoplethysmography (PPG) measurement. The PPG measurement may be a measurement of blood volume of a user operating the mobile device 100. The PPG measurement may be obtained by the PPG measurement module 192 in response to a user action. The PPG measurement module 192 may interface with the light source 185 and light sensors 182 in order to obtain the PPG measurement. Upon indication by the user of a need for a PPG measurement, the PPG measurement module 192 may direct the light source 185, or multiple light sources, to emit light through the user's body. As described above, the emitted light may reflect off or transmitted through blood vessels within the user's body and may be detected by one or more light sensors 182 within the mobile device 100. The PPG measurement module 192 may measure, by interfacing with the one or more light sensors, the amount of reflected or transmitted light detected by the one or more light sensors 182. The PPG measurement module 192 may then determine a PPG measurement that is indicative of the user's blood volume based on the measurement of the reflected light.

ECG measurement module 194 is configured to, when executed by processor 110, obtain an electrocardiography (ECG) measurement. The ECG measurement may be a measurement of heart electrical activity of a user operating the mobile device 100. The ECG measurement may be obtained by the ECG measurement module 194 in response to a user action. The ECG measurement module 194 may interface with the electrodes 184 in order to obtain the ECG measurement. Upon indication by the user of a need for an ECG measurement, the ECG measurement module 194 may interface with the electrodes 184 to measure (assuming the user's body completes a circuit between the electrodes 184) electrical impulse(s) generated by the polarization and depolarization of cardiac tissue within the user's body. In some embodiments, the electrical impulse(s) may be generated by the beating of the user's heart. In some embodiments, the ECG measurement module 194 may interface with the electrodes 184 to measure the electrical impulse(s) automatically upon the user's body completing a circuit between the electrodes 184. The ECG measurement module 194 may then determine an ECG measurement based on the measured electrical impulse(s). It can be appreciated that ECG measurement can be obtained using two or more electrode leads.

Blood pressure measurement module 196 is configured to, when executed by processor 110, generate a blood pressure measurement of the user based on the PPG measurement and the ECG measurement. According to Poon, C. C. Y.; Zhang, Y. T. "Cuff-less and Noninvasive Measurements of Arterial Blood Pressure by Pulse Transit Time", *Engineering in Medicine and Biology* 27$^{th}$ *Annual Conference*, 2005. *IEEE*, On page(s): 1-4, the calculation of the blood pressure measurement based on the PPG measurement and the ECG measurement is well known in the art.

Impedance measurement module 198 is configured to, when executed by processor 110, obtain an impedance measurement. The impedance measurement may be indicative of a hydration level of a user operating the mobile device 100. The impedance measurement may be obtained by the impedance measurement module 198 in response to a user action. In impedance measurement module 198 may interface with the electrodes 184 in order to obtain the impedance measurement. Upon indication by the user of a need for an impedance measurement, the impedance measurement module 198 may interface with the electrodes 184 to measure (assuming the user's body completes a circuit between the electrodes 184) electrical impedance through the user's body. In some embodiments, the impedance measurement module 198 may interface with the electrodes 184 to measure the electrical impedance automatically upon the user's body completing a circuit between the electrodes 184.

Hydration level measurement module 199 is configured to, when executed by processor 110, obtain a hydration level measurement based on the impedance measurement obtained by the impedance measurement module 198. The hydration level measurement module 199 may determine the hydration level from the measured impedance using techniques well known in the art.

It can be appreciated that the outer body of the mobile device 100 may be sized to be portable for a user. It can be appreciated that the term "portable" may refer to something that is able to be easily carried or moved, and may be a light and/or small. In the context of embodiments of the present invention, the term portable may refer to something easily transportable by the user or wearable by the user. For example, the mobile device 100 may be a smartphone device or a watch wearable by the user. Other examples of portable devices include a head-mounted display, calculator, portable media player, digital camera, pager, personal navigation device, etc. Examples of devices that may not be considered portable include a desktop computer, traditional telephone, television, appliances, etc. It can be appreciated that the bodily function measurements can be obtained via the smartphone, watch, or any other of the mentioned devices.

Figure 2:
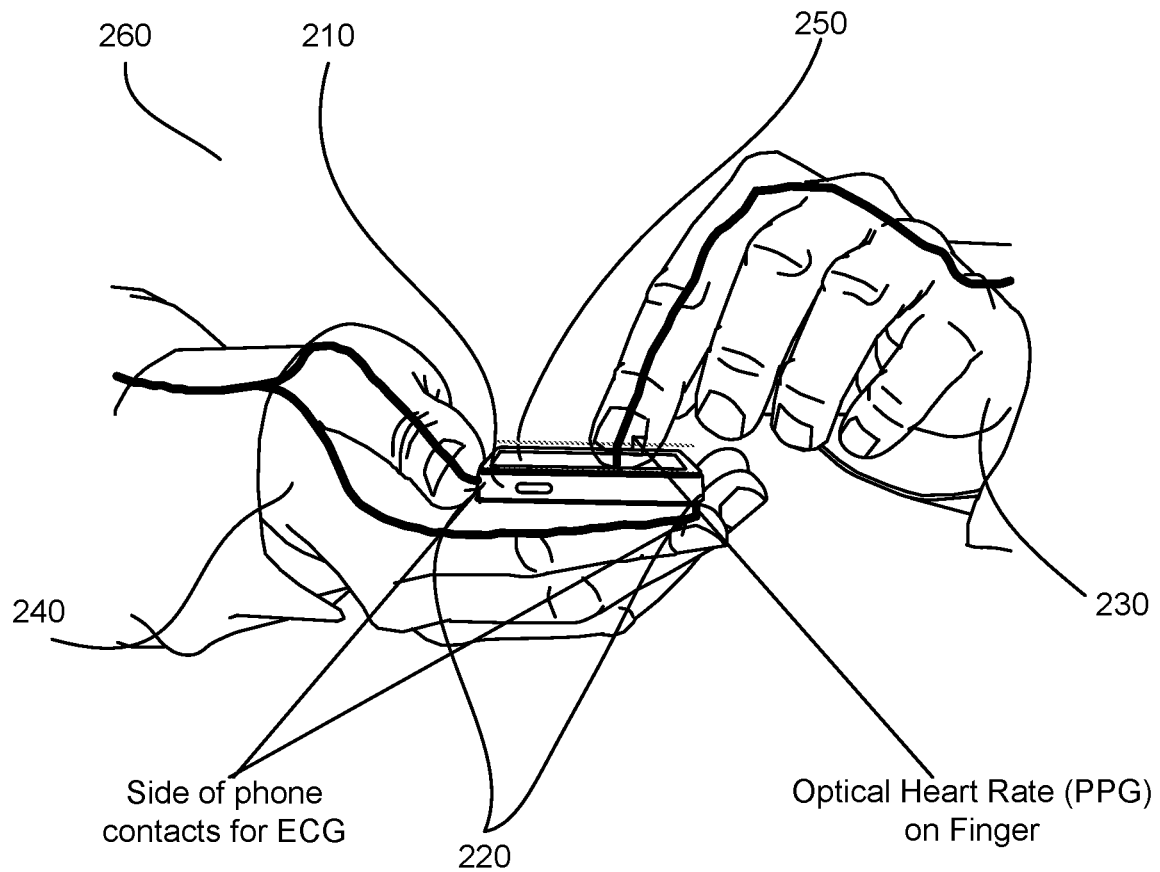
FIG. 2 illustrates a smartphone device configured to obtain PPG and ECG measurements of a user, according to some embodiments.

FIG. 2 illustrates a smartphone device 210 configured to obtain PPG and ECG measurements of a user, according to some embodiments. It can be appreciated that the smartphone device 210 is only one example of a mobile device 100. The smartphone device 210 may include a plurality of contacts 220. In some embodiments, a single contact 220 may be positioned at each end of the smartphone device 210.

In other embodiments, a device front surface 250 of the smartphone device 210 may include a contact layer including, e.g., silver metal or Indium Tin Oxide (ITO). The smartphone device 210 may obtain both PPG and ECG measurements of the user 260. In some embodiments, the device front surface 250 may be a touchscreen.

For example, the user 260 may hold the smartphone device 210 with his/her first hand 240 touching one or more of the contacts 220 and with his/her second hand 230 touching the device front surface 250. Upon the user 260 performing this action, the contacts 220 and the contact layer of the device front surface 250 may complete a circuit through the user's 260 body. The smartphone device 210 may then measure an electrical potential through the completed circuit to determine the ECG measurement. It can be appreciated that the ECG measurement may also be obtained without the user's first hand 240 or second hand 230 contacting the device front surface 250. That is, the user's first hand 240 may make contact with a first side contact 220 and the user's second hand 230 may make contact with a second side contact 220 to complete the circuit. Alternatively, the user 260 may make contact with both side contacts 220 using only his/her first hand 240 or second hand 230 (see below for a measurement of PPG or Galvanic Skin Response (GSR)). Alternatively, and not illustrated in FIG. 1, sensors positioned and/or touched at other locations, for example legs, feet, ankles, knees, elbows, arms, neck, head, etc. could also be used to generate PPG, GSR and possibly ECG, depending on the location and how the contact was made.

The device front surface 250 of the smartphone device 210 may also obtain a PPG measurement of the user 260 by using an optical based technology. For example, when the user 260 touches the device front surface 250, the touchscreen may shine a light into the user's 260 skin, measure the blood flow through the capillaries and thus determine a heart rate (PPG) of the user. This process is described in further detail below.

Accordingly, by obtaining both the PPG and ECG measurements of the user 260, a PTT technique may be used to determine the user's blood pressure. The smartphone device 210 may then provide important information to the user 260, based on the determined blood pressure (described further below).

Additionally, the smartphone device 210 may obtain an impedance measurement of the user using BIA techniques. In some embodiments, the impedance measurement may be obtained via the contact layer of the device front surface 250. The process of obtaining the impedance measurement is described in further detail below.

It can be appreciated that the device front surface 250 may serve multiple functions. That is, the device front surface 250 may be used to obtain ECG, PPG, and/or impedance measurements as described above, and may also be used as a user input device. The user 260 may use the device front surface 250 to provide input to applications being executed on the smartphone device 210. When the user 260 wishes to obtain a bodily function measurement using the device front surface 250, the user 260 may place the smartphone device 210 into a measurement mode. Alternatively, the smartphone device 210 may automatically detect the user's intention to obtain a bodily function measurement, e.g., from the user 260 placing his/her finger in a particular location on the device front surface 250 or touching the device front surface 250 for a predetermined period of time. Alternatively, the smartphone device 210 may regularly scan and store vital signs of the user 260 in the user's normal course of operating the device 210, without the user wanting or needed a particular vital sign report at that time.

Figure 3:
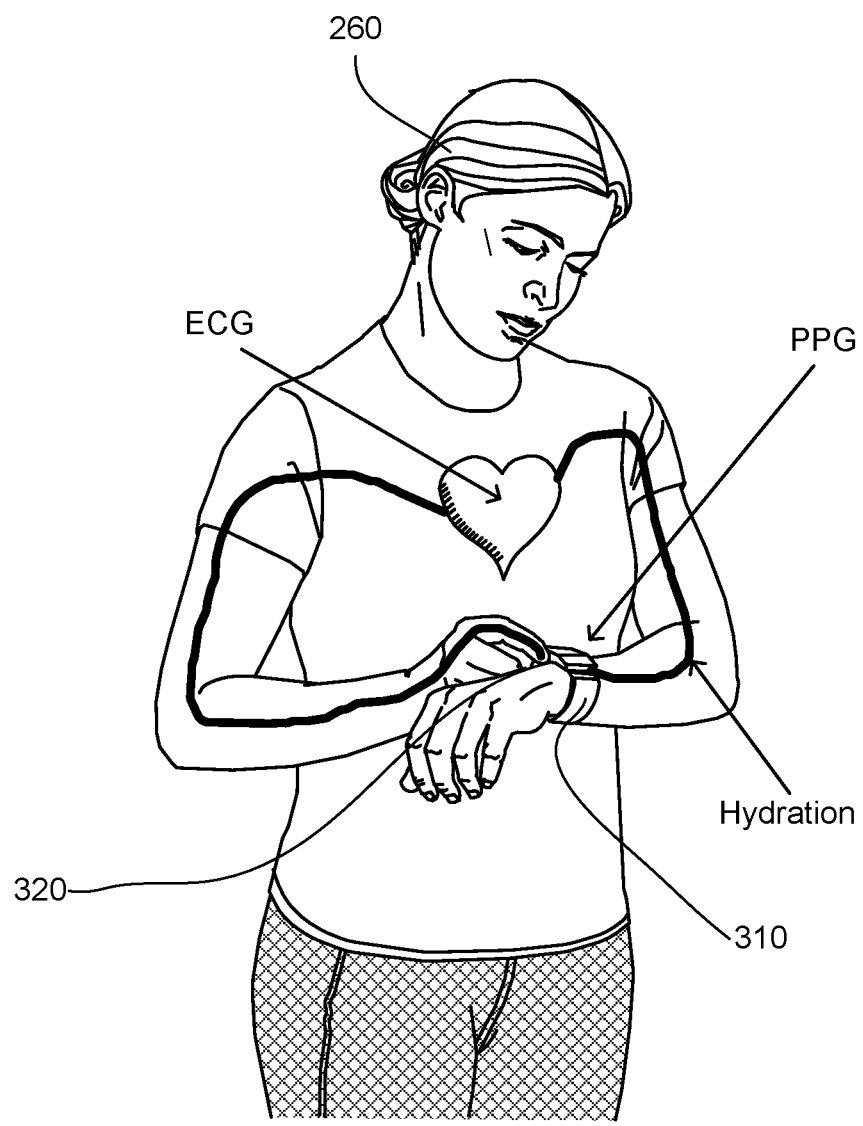
FIG. 3 illustrates a wristwatch device configured to obtain PPG, ECG, and impedance measurements of a user, according to some embodiments.

FIG. 3 illustrates a wristwatch device 310 configured to obtain PPG, ECG, and impedance measurements of a user, according to some embodiments. The wristwatch device 310 illustrated in FIG. 3 operates similarly to the smartphone device 210 in FIG. 2. That is, the wristwatch device 310 may obtain PPG, ECG, and impedance measurements of the user 260 via a plurality of contacts. In some embodiments, one or more contacts may be placed at the bottom of the wristwatch device 310, where the contact makes a continuous contact with the user's 260 wrist while the user 260 wears the wristwatch device 310.

The wristwatch device 310 may also include a multifunction button 320, which may be used to obtain a bodily function measurement and also as a user input device. For example, the multifunction button 320 may be used by the user 260 to set a date and/or time for the wristwatch device 310. The multifunction button may have an integrated electrode on the surface. The user 260 may also use the multifunction button 320 to obtain an ECG measurement by touching the button 320 to complete a circuit (via the other contacts) through the user's body. In some embodiments, the multifunction button 320 may be integrated into a touch-screen of the wristwatch device 310.

The PPG and hydration measurements may be obtained in a similar fashion as described with respect to the smartphone device of FIG. 2, e.g., via the contacts on the wristwatch device 310. The PPG measurement may also be obtained using optical techniques, as described below.

The wristwatch device 310 may be designed to be portable such that the user may easily wear the device or carry it on his/her person. In some embodiments, the wristwatch device 310 may perform everyday functions other than obtaining PPG, ECG, and impedance measurements of the user. For example, the wristwatch device 310 may provide the current time, a stopwatch function, a calendar function, communication functions, etc. The PPG, ECG, and impedance measurements functions may be available in addition to the other described functions on the wristwatch device 310.

Figure 4:
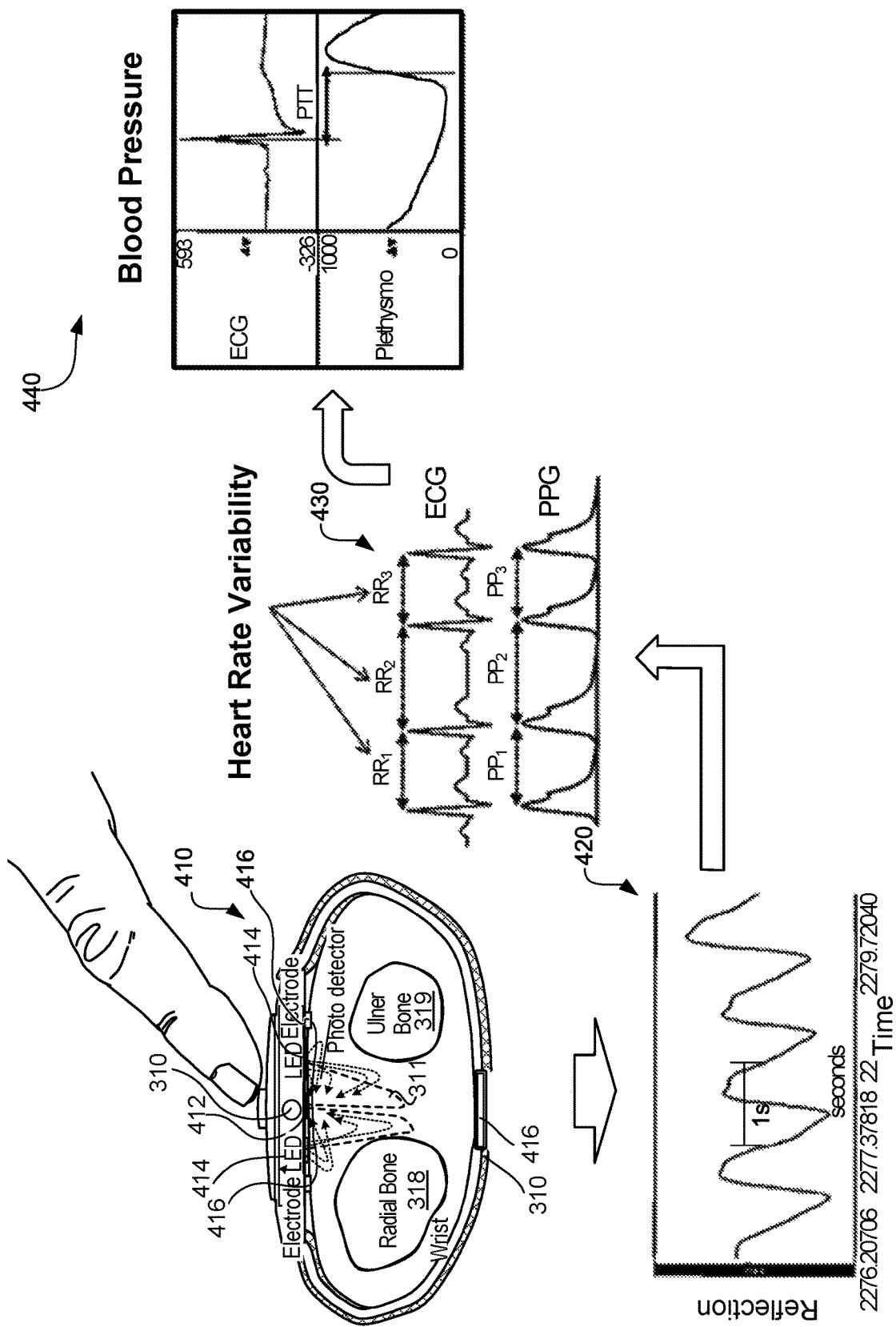
FIG. 4 illustrates a cross sectional view of the wristwatch device of FIG. 3 and graphs showing measurements obtained by the wristwatch device, according to some embodiments.

FIG. 4 illustrates a cross sectional view 410 of the wristwatch device 310 of FIG. 3 and graphs 420, 430, and 440 showing measurements obtained by the wristwatch device, according to some embodiments. The cross sectional view 410 of the wristwatch device 310 shows a photodetector 412, a plurality of light emitting diodes (LED) 414, and a plurality of electrodes contacts 416. Additionally, the cross sectional view 410 also illustrates parts of a user's wrist, e.g., radial bone 418 and ulnar bone 419.

The wristwatch device 310 may obtain PPG measurements of the user by using optical techniques. To obtain a PPG measurement, the LEDs 414 (typically positioned at the bottom of the wristwatch device 310 and on top of the user's wrist) may emit a light into the user's skin. The reflected light may be received at the photodetector 412. The user's blood volume may be determined based off of the reflected light as compared against time. From this data, the user's PPG measurement may be determined. In some embodiments, the determination of the user's blood volume may be determined from a change in the user's blood volume. More specifically, a change in the diameter of the blood vessels that are being probed by the LEDs 414.

Additionally, the user's ECG measurement may be obtained using the plurality of contacts 416 as described above with respect to FIG. 3. It can be appreciated that in the wristwatch device 310 embodiment, the plurality of contacts 416 may continuously be in contact with the user's skin while the user is wearing the wristwatch device 310 around his/her wrist. The user may then touch, with his/her hand that is not wearing the wristwatch device 310, another contact 416 that is located at another location on the wristwatch device 310 to complete the circuit through the user's body.

Similarly, the user's hydration measurements may also be obtained by using the plurality of contacts 416 and determining impedance through the user's body.

Graph 420 illustrates the intensity of the obtained light reflections at the photodetector 412 against time. In this example, the duration between each pulse is approximately one second. From this graph, the user's PPG can be determined.

Graph 430 shows a user's heart rate variability by comparing the user's ECG and the user's PPG. As shown in graph 440, the PTT can be determined by taking the difference between a peak of an ECG pulse and the corresponding inflection point (at the same time interval) of the PPG pulse. The PTT may then be used to determine the user's blood pressure, which is well known in the art.

Figure 5:
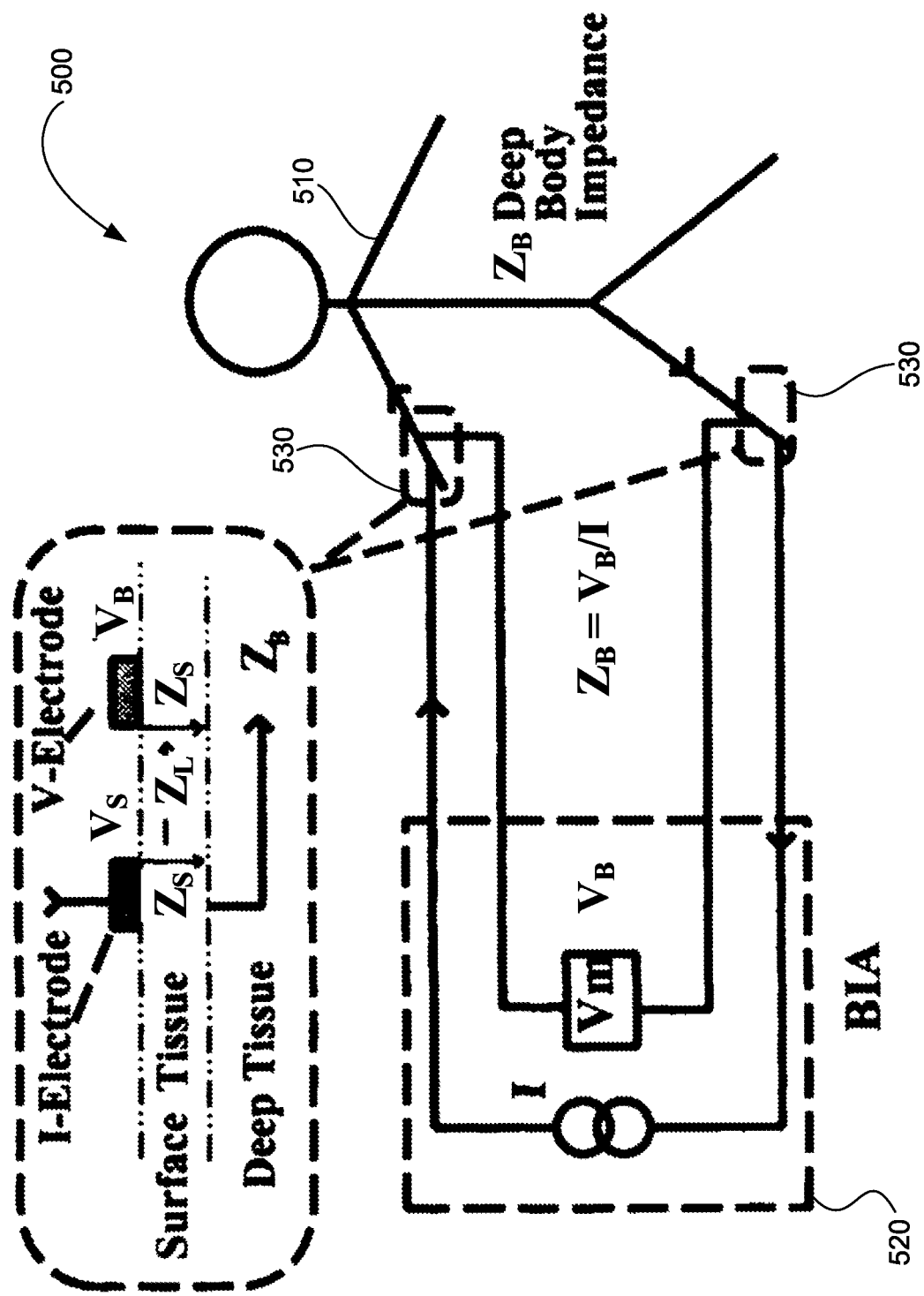
FIG. 5 a schematic diagram of a mobile device configured to obtain impedance measurements of a user, according to some embodiments.

FIG. 5 is a schematic diagram 500 of a mobile device configured to obtain impedance measurements of a user, according to some embodiments. The mobile device may be either the smartphone device described in FIG. 2, the wristwatch device described in FIG. 3, or any other mobile device. As described above, the impedance measurement of the user may be used to determine the user's hydration level using BIA techniques. The user's body 510 essentially functions as a capacitance and resistance network in this illustration. When the user's body 510 makes contact with the contact points 530, an impedance converter 520 may determine the impedance value through the user's body 510. In this scenario, the user's body 510 may act as a capacitor. The impedance value may be a function of surface tissue impedance and deep tissue impedance. The impedance value may then be used to estimate a total body water content of the user's body 510. This figure shows measuring the impedance through one leg, the torso, and one arm. The method works the same way measuring through both arms and the chest. In some embodiments, the mobile device may include phase-sensitive electronics to distinguish between electrical resistance and reactance.

Upon determining the user's hydration level, the mobile device may provide a notification to the user. The types of notifications are described in further detail with respect to FIG. 7.

Figure 6:
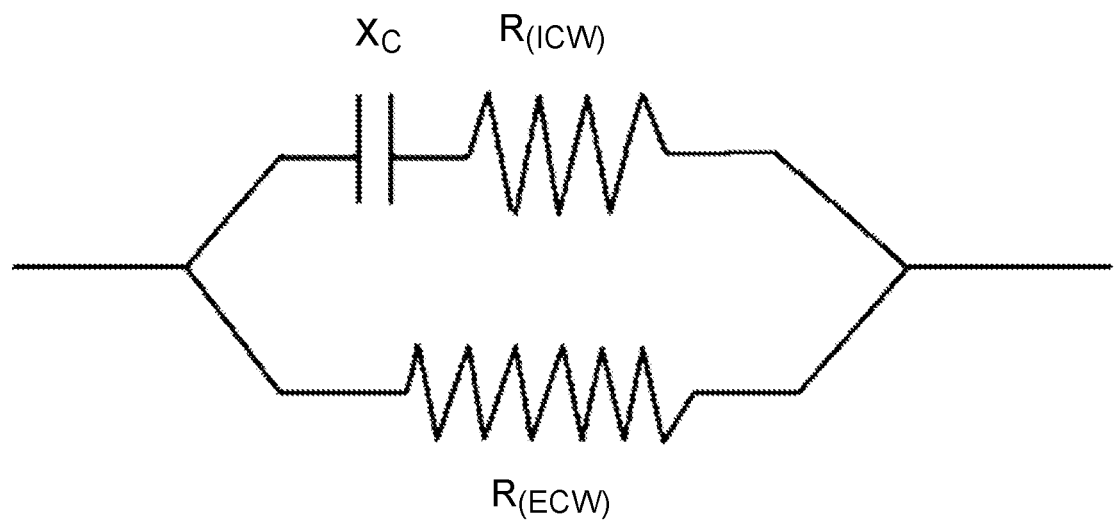
FIG. 6 is a schematic diagram of two resistors and a capacitor representing conduction through tissue, according to some embodiments.

FIG. 6 is a schematic diagram 600 of two resistors and a capacitor representing conduction through tissue, according to some embodiments. In FIG. 6, $x_c$ represents the capacitance of the user's cell walls, $R_{(ICW)}$ represents the resistance of the body water inside of the user's cells, and $R_{(ECW)}$ represents the resistance of the body water outside of the user's cells. The circuit shown in FIG. 6 may be used as part of the schematic diagram in FIG. 5 to determine the hydration level of the user by determining an electrical impedance through the user's body.

Figure 7:
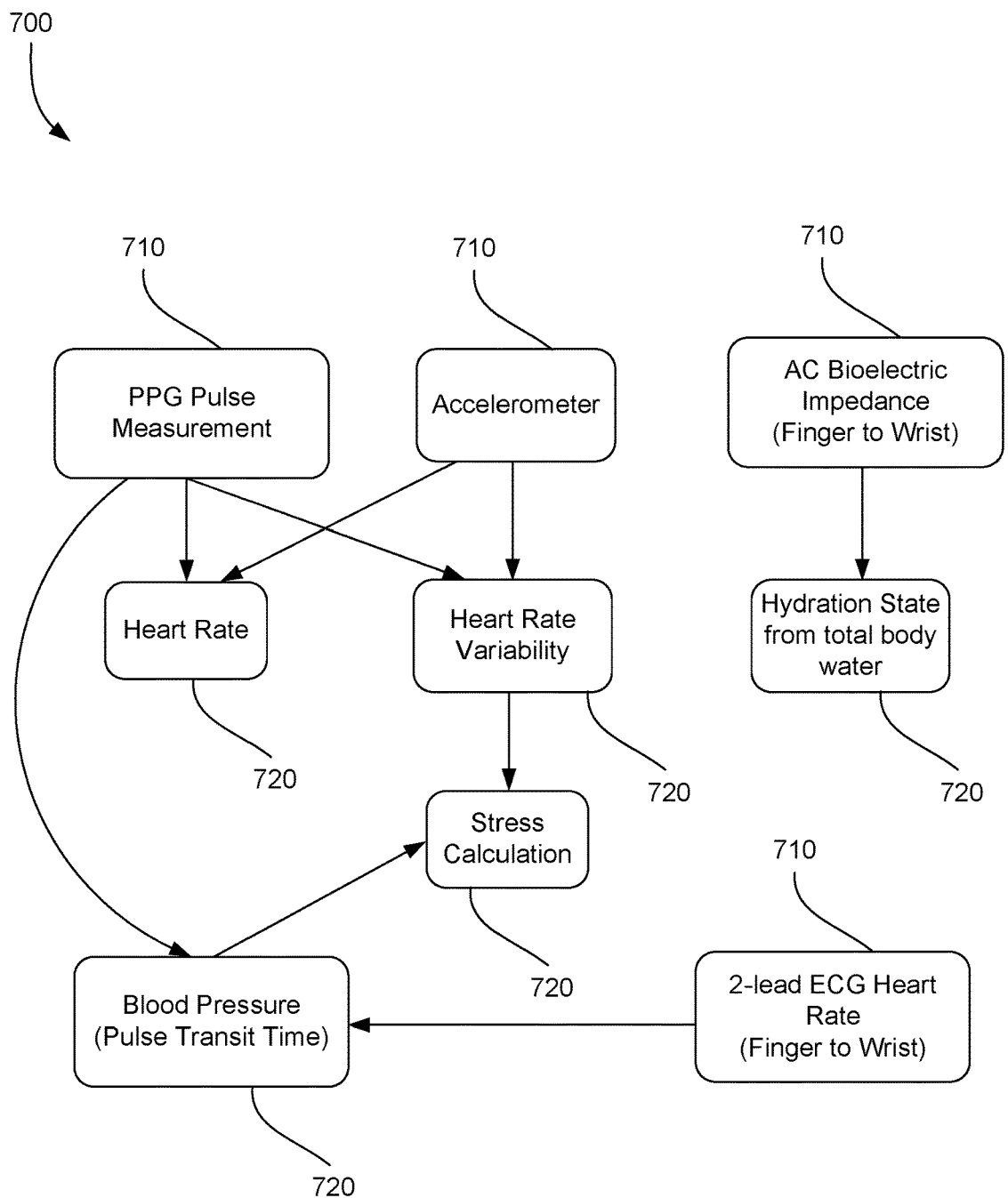
FIG. 7 is a flow diagram illustrating a plurality of derived metrics from a plurality of sensor metrics, according to some embodiments.

FIG. 7 is a flow diagram 700 illustrating a plurality of derived metrics 720 from a plurality of sensor metrics 710, according to some embodiments. The plurality of sensor metrics 710 may include, but is not limited to, PPG pulse measurement, accelerometer measurements, AC biometric impedance measurements, and 2-lead ECG heart rate measurements. These sensor metrics 710 may be obtained by taking measurements via the mobile device. Based on data from the sensor metrics 710, a plurality of derived metrics 720 may be derived. These derived metrics may include, but is not limited to, heart rate, heart rate variability, stress calculation, blood pressure, and hydration state.

For example, when a PPG pulse measurement is obtained, using the techniques described herein, the user's heart rate and/or heart rate variability may be determined. The PPG pulse measurement may be combined with an ECG heart rate measurement to determine the user's blood pressure using PTT techniques. Based on the determined blood pressure, a user's stress level may be determined. If it is determined that the user is at a high stress level, the mobile device may notify the user to take a deep breath, go for a walk, drink a glass of water, etc. As shown, the stress level may also be determined from the user's GSR data.

In another example, when an AC bioelectric impedance measurement is obtained, using the techniques described herein, the user's hydration state may be determined from data regarding the total body water of the user. If the user's hydration state is determined to be low, the mobile device may notify the user to drink a glass of water. On the other hand, if the user's hydration state is determined to be adequate, the mobile device may notify the user that to keep up the good work.

In another example, energy calculations may be determined based upon accelerometer and gyroscope data obtained by the mobile device. For example, if the user is moving around actively, the accelerometer data may indicate a high level of movement and the mobile device may determine that the user's energy level is high. The mobile device may notify the user to continue being active. In some embodiments, the mobile device may keep track of the user's energy level throughout the day and notify the user upon predetermined intervals to become active in order to reach a threshold amount of activity for the day.

In some embodiments, accelerometer measurements may be used to determine the user's heart rate and/or heart rate variability. The same calculations described above may determined/calculated using these measurements.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Moreover, nothing disclosed herein is intended to be dedicated to the public.

Figure 8:
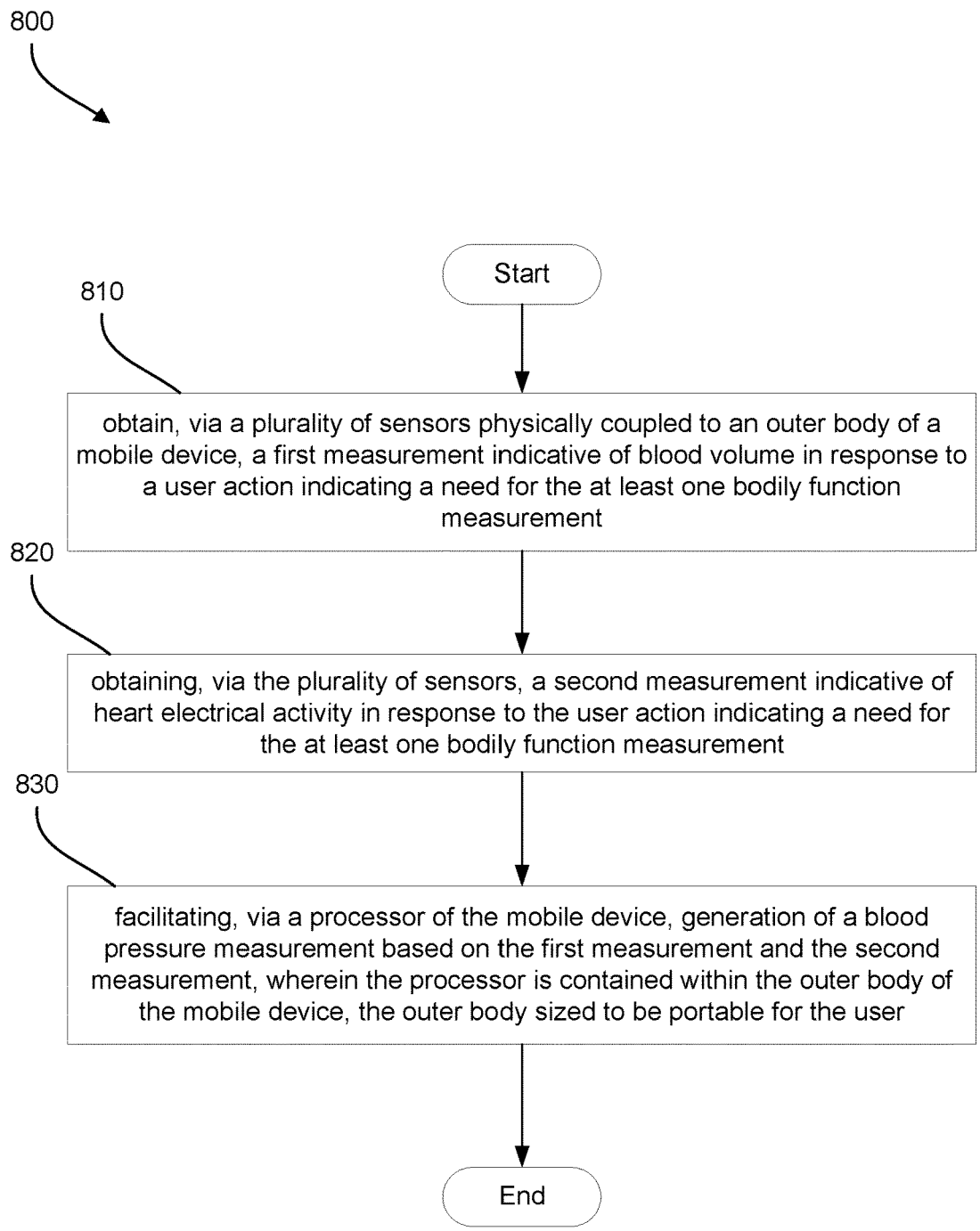
FIG. 8 is a flow diagram of an exemplary method of obtaining at least one bodily function measurement.

FIG. 8 is a flow diagram 800 of an exemplary method of obtaining at least one bodily function measurement. In block 810, a first measurement indicative of blood volume is obtained in response to a user action. The first measurement may be obtained via a plurality of sensors physically coupled to an outer body of a mobile device. In some embodiments, the first measurement may be a photoplethysmography (PPG) measurement.

In some embodiments, the plurality of sensors may include at least one light sensor. The mobile device may also include at least one light source. Obtaining the first measurement may include measuring, via the at least one light sensor, reflected light from the light source reflected off of blood vessels within a user of the mobile device. For example, in FIG. 3, the wearable watch obtains a PPG measurement of the user via the light sensors and light source within the wearable watch. The PPG measurement may be obtained by the PPG measurement module described in FIG. 1.

In block 820, a second measurement indicative of heart electrical activity is obtained in response to the user action. The second measurement may be obtained via the plurality of sensors. In some embodiments, the second measurement may be an electrocardiography (ECG) measurement.

In some embodiments, the plurality of sensors may include at least a first electrode and a second electrode. Obtaining the second measurement may include detecting completion of a circuit between the first electrode and the second electrode via a portion of the user's body. For example, in FIG. 3, the wearable watch obtains an ECG measurement of the user via the electrodes located on the outer body of the wearable watch. The ECG measurement may be obtained by the ECG measurement module described in FIG. 1.

In block 830, generation of a blood pressure measurement based on the first measurement and the second measurement is facilitated via a processor of the mobile device. The processor may be contained within the outer body of the mobile device and the outer body may be sized to be portable for the user. In some embodiments, the mobile device may be configured to perform a primary function and a secondary function. Facilitating the generation of the blood pressure measurement may be performed as the secondary function of the mobile device. For example, in FIG. 3, the wearable watch may facilitate measurement of the user's blood pressure based on the obtained PPG and ECG measurements. The blood pressure may be determined by the blood pressure measurement module described in FIG. 1.

In some embodiments, the mobile device is a watch. For example, in FIG. 3, the mobile device is a wearable watch. In other embodiments, the mobile device is a smartphone device. For example, in FIG. 2, the mobile device is a smartphone device.

In some embodiments, at least one of the sensors is built into a multifunction surface, wherein the multifunction surface is configured to simultaneously obtain the first measurement or the second measurement and a user input. For example, in FIG. 2, the smartphone device (also capable of obtaining PPG and ECG measurements similar to the wearable watch) includes a multifunction touchscreen surface that facilitates user input to the smartphone device.

In some embodiments, block 810 and block 820 may be performed by a first device and block 830 may be performed by a second device. That is, the measures of blood volume and heart electrical activity may be performed by a device separate than the generation of the blood pressure measurement. For example, the measure of blood volume and heart electrical activity may be performed via a communication device worn by the user, whereas the generation of the blood pressure measurement may be performed by a server computer that receives the measures of blood volume and heart electrical activity from the communication device. In some embodiments, the server computer could reside within a cloud system.

Figure 9:
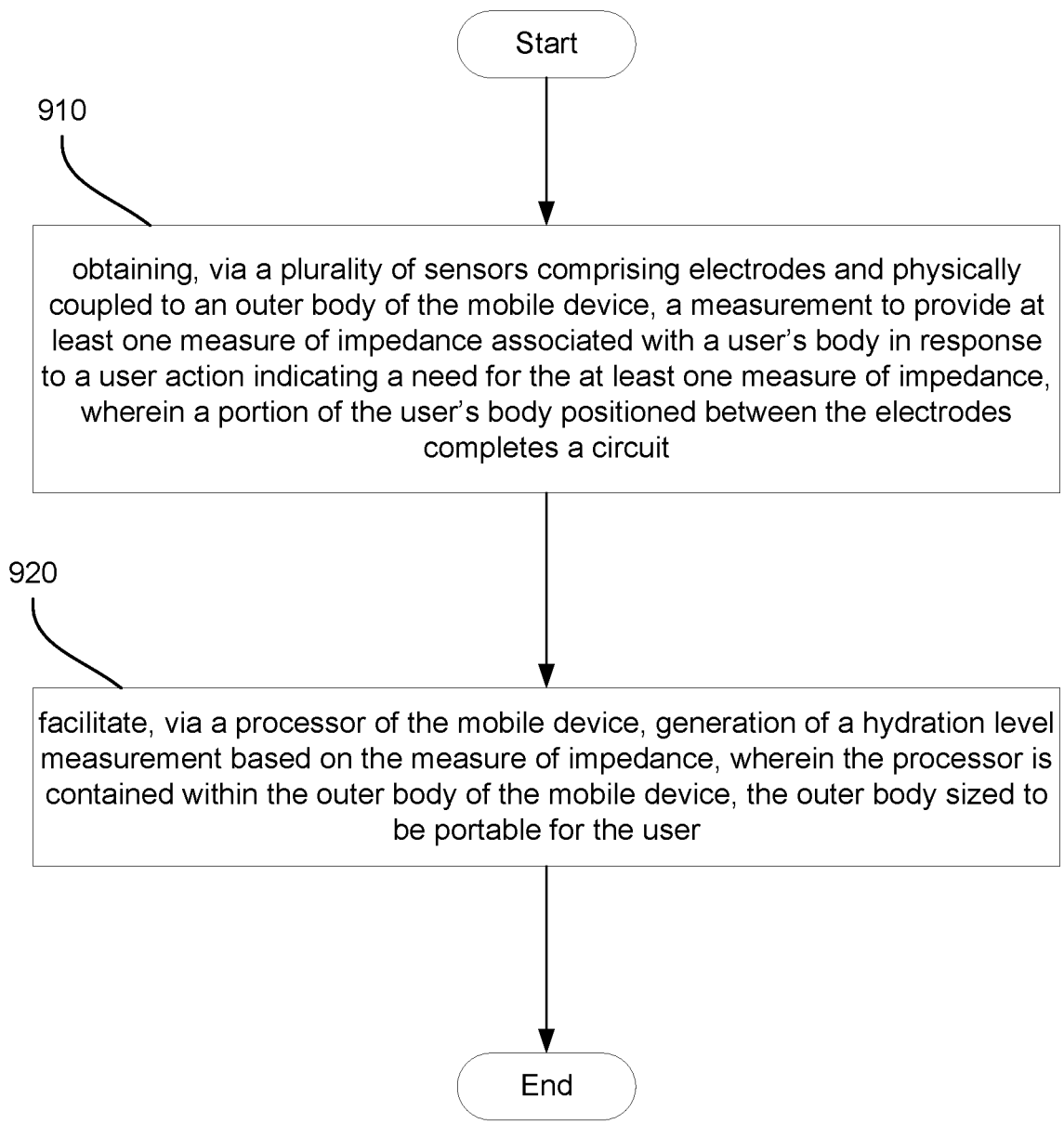
FIG. 9 is another flow diagram of an exemplary method of obtaining at least one bodily function measurement.

FIG. 9 is another flow diagram 900 of an exemplary method of obtaining at least one bodily function measurement. In block 910, a measurement to provide at least one measure of impedance associated with a user's body is obtained in response to a user action. In some embodiments, the measurement may be obtained via a plurality of sensors comprising electrodes that are physically coupled to an outer body of the mobile device. In some embodiments, a portion of the user's body positioned between the electrodes completes a circuit.

For example, in FIG. 3, the wearable watch obtains an impedance measurement of the user via the electrodes located on the outer body of the wearable watch. The impedance measurement may be obtained by the impedance measurement module described in FIG. 1.

In block 920, generation of a hydration level measurement based on the measure of impedance is facilitated via a processor of the mobile device. In some embodiments, the processor is contained within the outer body of the mobile device. In some embodiments, the outer body is sized to be portable for the user.

In some embodiments, the mobile device is configured to perform a primary function and a secondary function. In some embodiments, the processor is configured to facilitate generation of the hydration level measurement as the secondary function of the mobile device. For example, in FIG. 3, the wearable watch may facilitate measurement of the user's hydration level based on the obtained impedance measurement. The hydration level may be determined by the hydration level measurement module described in FIG. 1.

In some embodiments, at least one of the sensors is built into a multifunction surface. In some embodiments, the multifunction surface is configured to simultaneously obtain the impedance measurement and a user input. In some embodiments, the multifunction surface comprises Indium Tin Oxide (ITO). In some embodiments, the multifunction surface comprises silver metal. In some embodiments, the multifunction surface comprises a network of wires or a transparent conductor. For example, in FIG. 2, the smartphone device (also capable of obtaining impedance measurements similar to the wearable watch) includes a multifunction touchscreen surface that facilitates user input to the smartphone device.

In some embodiments, the mobile device is a watch. For example, in FIG. 3, the mobile device is a wearable watch. In other embodiments, the mobile device is a smartphone device. For example, in FIG. 2, the mobile device is a smartphone device.

In some embodiments, block 910 may be performed by a first device and block 920 may be performed by a second device. That is, the measure of impedance may be performed by a device separate than the generation of the hydration level measurement. For example, the measure of impedance may be performed via a communication device worn by the user, whereas the generation of the hydration level may be performed by a server computer that receives the measure of impedance from the communication device. In some embodiments, the server computer could reside within a cloud system.

Figure 10:
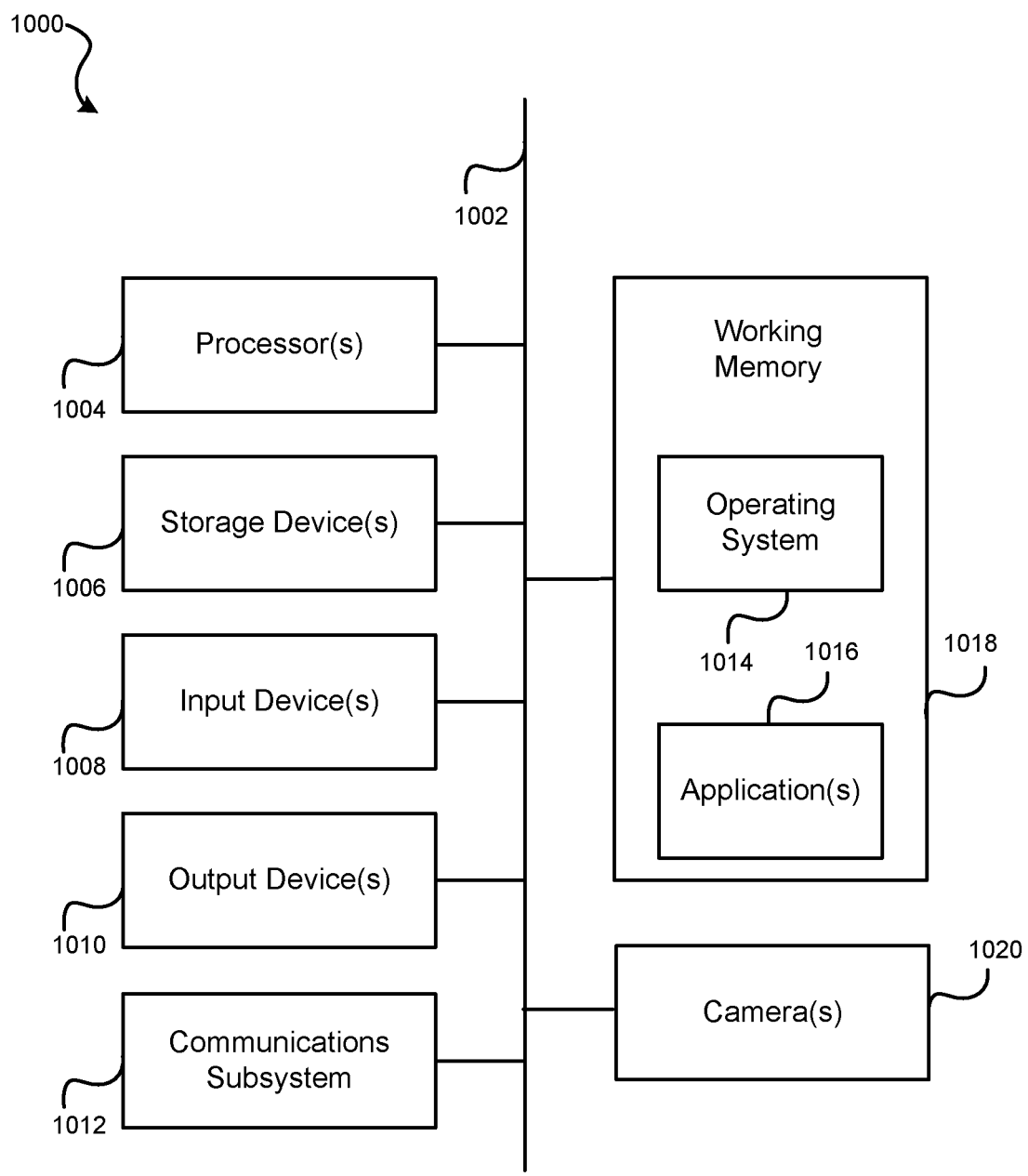
FIG. 10 illustrates an example of a computing system in which one or more embodiments may be implemented.

FIG. 10 illustrates an example of a computing system in which one or more embodiments may be implemented. A computer system as illustrated in FIG. 10 may be incorporated as part of the above described computerized device. For example, computer system 1000 can represent some of the components of a television, a computing device, a server, a desktop, a workstation, a control or interaction system in an automobile, a tablet, a netbook or any other suitable computing system. A computing device may be any computing device with an image capture device or input sensory unit and a user output device. An image capture device or input sensory unit may be a camera device. A user output device may be a display unit. Examples of a computing device include but are not limited to video game consoles, tablets, smart phones and any other hand-held devices. FIG. 10 provides a schematic illustration of one embodiment of a computer system 1000 that can perform the methods provided by various other embodiments, as described herein, and/or can function as the host computer system, a remote kiosk/terminal, a point-of-sale device, a telephonic or navigation or multimedia interface in an automobile, a computing device, a set-top box, a table computer and/or a computer system. FIG. 10 is meant only to provide a generalized illustration of various components, any or all of which may be utilized as appropriate. FIG. 10, therefore, broadly illustrates how individual system elements may be implemented in a relatively separated or relatively more integrated manner. In some embodiments, elements of computer system 100 may be used to implement functionality of the mobile device 100 in FIG. 1.

The computer system 1000 is shown comprising hardware elements that can be electrically coupled via a bus 1002 (or may otherwise be in communication, as appropriate). The hardware elements may include one or more processors 1004, including without limitation one or more general-purpose processors and/or one or more special-purpose processors (such as digital signal processing chips, graphics acceleration processors, and/or the like); one or more input devices 1008, which can include without limitation one or more cameras, sensors, a mouse, a keyboard, a microphone configured to detect ultrasound or other sounds, and/or the like; and one or more output devices 1010, which can include without limitation a display unit such as the device used in embodiments of the invention, a printer and/or the like.

In some implementations of the embodiments of the invention, various input devices 1008 and output devices 1010 may be embedded into interfaces such as display devices, tables, floors, walls, and window screens. Furthermore, input devices 1008 and output devices 1010 coupled to the processors may form multi-dimensional tracking systems.

The computer system 1000 may further include (and/or be in communication with) one or more non-transitory storage devices 1006, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including without limitation, various file systems, database structures, and/or the like.

The computer system 1000 might also include a communications subsystem 1012, which can include without limitation a modem, a network card (wireless or wired), an infrared communication device, a wireless communication device and/or chip set (such as a Bluetooth™ device, an 802.11 device, a Wi-Fi device, a WiMax device, cellular communication facilities, etc.), and/or the like. The communications subsystem 1012 may permit data to be exchanged with a network, other computer systems, and/or any other devices described herein. In many embodiments, the computer system 1000 will further comprise a non-transitory working memory 1018, which can include a RAM or ROM device, as described above.

The computer system 1000 also can comprise software elements, shown as being currently located within the working memory 1018, including an operating system 1014, device drivers, executable libraries, and/or other code, such as one or more application programs 1016, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 1006 described above. In some cases, the storage medium might be incorporated within a computer system, such as computer system 1000. In other embodiments, the storage medium might be separate from a computer system (e.g., a removable medium, such as a compact disc), and/or provided in an installation package, such that the storage medium can be used to program, configure and/or adapt a general purpose computer with the instructions/code stored thereon. These instructions might take the form of executable code, which is executable by the computer system 1000 and/or might take the form of source and/or installable code, which, upon compilation and/or installation on the computer system 1000 (e.g., using any of a variety of generally available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed. In some embodiments, one or more elements of the computer system 1000 may be omitted or may be implemented separate from the illustrated system. For example, the processor 1004 and/or other elements may be implemented separate from the input device 1008. In one embodiment, the processor is configured to receive images from one or more cameras that are separately implemented. In some embodiments, elements in addition to those illustrated in FIG. 10 may be included in the computer system 1000.

Some embodiments may employ a computer system (such as the computer system 1000) to perform methods in accordance with the disclosure. For example, some or all of the procedures of the described methods may be performed by the computer system 1000 in response to processor 1004 executing one or more sequences of one or more instructions (which might be incorporated into the operating system 1014 and/or other code, such as an application program 1016) contained in the working memory 1018. Such instructions may be read into the working memory 1018 from another computer-readable medium, such as one or more of the storage device(s) 1006. Merely by way of example, execution of the sequences of instructions contained in the working memory 1018 might cause the processor(s) 1004 to perform one or more procedures of the methods described herein.

The terms "machine-readable medium" and "computer-readable medium," as used herein, refer to any medium that participates in providing data that causes a machine to operate in a specific fashion. In some embodiments implemented using the computer system 1000, various computer-readable media might be involved in providing instructions/code to processor(s) 1004 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 1006. Volatile media include, without limitation, dynamic memory, such as the working memory 1018. Transmission media include, without limitation, coaxial cables, copper wire and fiber optics, including the wires that comprise the bus 1002, as well as the various components of the communications subsystem 1012 (and/or the media by which the communications subsystem 1012 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a floppy disk, a flexible disk, hard disk, magnetic tape, or any other magnetic medium, a CD-ROM, any other optical medium, punch-cards, papertape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to the processor(s) 1004 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 1000. These signals, which might be in the form of electromagnetic signals, acoustic signals, optical signals and/or the like, are all examples of carrier waves on which instructions can be encoded, in accordance with various embodiments of the invention.

The communications subsystem 1012 (and/or components thereof) generally will receive the signals, and the bus 1002 then might carry the signals (and/or the data, instructions, etc. carried by the signals) to the working memory 1018, from which the processor(s) 1004 retrieves and executes the instructions. The instructions received by the working memory 1018 may optionally be stored on a non-transitory storage device 1006 either before or after execution by the processor(s) 1004.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A wearable device for obtaining at least one bodily function measurement, comprising:
    an outer body shaped as a part of a wristwatch and configured to be wearable by a user on the user's wrist adjacent to a first hand of the user;
    a plurality of sensors physically coupled to the outer body, a first sensor of the plurality of sensors comprising a first electrode coupled to the outer body, the first electrode positioned to be contacted by the user's wrist; and
    a multifunction contact button comprising a second electrode of the first sensor, wherein the multifunction contact button is coupled to the outer body and positioned to be contacted by a finger or thumb of a second hand of the user, the multifunction contact button capable of (i) receiving user input to interact with the wearable device, (ii) transitioning the wearable device from a normal course of operation to a measurement mode and initiating an electrocardiogram ("ECG") measurement, and (iii) transitioning the wearable device from the normal course of operation to a measurement mode and initiating a photoplethysmography ("PPG") measurement using a second sensor of the plurality of sensors, and is configured to, based on a contact, perform (i), (ii), (iii), or a combination thereof, wherein the measurement mode is activated based on a user interaction indicating a desire to obtain a bodily function measurement, and wherein the normal course of operation allows background ECG or PPG measurements; and
    a processor contained within the outer body and coupled to the plurality of sensors, the processor configured to, in response to the wearable device transitioning into a measurement mode, obtain the ECG measurement based on signals received from the first electrode and the second electrode or a PPG measurement based on signals received from the second sensor.

2. The wearable device of claim 1, wherein the processor configured to obtain the ECG measurement comprises the processor configured to:
    measure electrical impulses received by the first electrode and the second electrode; and
    determine the ECG measurement based on the measured electrical impulses.

3. The wearable device of claim 1, wherein the user input to interact with the wearable device comprises providing input to an application on the wearable device.

4. The wearable device of claim 1, wherein the user input to interact with the wearable device comprises non-sensor related activities.

5. The wearable device of claim 1, wherein the first electrode is coupled to a bottom of the wearable device.

6. The wearable device of claim 1, wherein processor configured to obtain the ECG measurement is performed in response to the user in contact with the first electrode and the second electrode.

7. The wearable device of claim 1, wherein the multifunction contact button is further used to obtain a hydration level measurement, the processor further configured to obtain the hydration level measurement based on the signals received from the first electrode and the second electrode.

8. A method for obtaining at least one bodily function measurement via a wearable device, comprising:
    receiving a user input to place the wearable device into a measurement mode, the wearable device comprising a multifunction contact button coupled to an outer body of the wearable device, the outer body shaped as a part of a wristwatch and configured to be wearable by a user on the user's wrist adjacent to a first hand of the user, the wearable device further comprising a plurality of sensors physically coupled to the outer body, a first sensor of the plurality of sensors comprising a first electrode coupled to the outer body, the first electrode positioned to be contacted by the user's wrist, and the multifunction contact button comprising a second electrode of the first sensor, the multifunction contact button positioned to be contacted by a finger or thumb of a second hand of the user, the multifunction contact button capable of (i) receiving user input to interact with the wearable device, (ii) transitioning the wearable device from a normal course of operation to a measurement mode and initiating an electrocardiogram ("ECG") measurement, and (iii) transitioning the wearable device from the normal course of operation to a measurement mode and initiating a photoplethysmography ("PPG") measurement using a second sensor of the plurality of sensors, and is configured to, based on a contact, perform (i), (ii), (iii), or a combination thereof, wherein the measurement mode is activated based on a user interaction indicating a desire to obtain a bodily function measurement, and wherein the normal course of operation allows background ECG or PPG measurements;
    in the measurement mode:
        receiving, by a processor of the wearable device, signals from the first electrode and the second electrode;
        receiving, by the processor of the wearable device, signals from a second sensor of the plurality of sensors; and obtaining, by the processor, an electrocardiography ("ECG") measurement based on the signals received from the first electrode and the second electrode and a photoplethysmography (PPG) measurement using the second sensor.

9. The method of claim 8, wherein obtaining the ECG measurement comprises:
measuring electrical impulses received by the first electrode and the second electrode; and
determining the ECG measurement based on the measured electrical impulses.

10. The method of claim 8, further comprising receiving further user input, via the multifunction contact button, to an application on the wearable device.

11. The method of claim 8, wherein the user input to interact with the wearable device comprises non-sensor related activities.

12. The method of claim 8, wherein the first electrode is coupled to a bottom of the wearable device.

13. The method of claim 8, further comprising obtaining the ECG measurement in response to the user in contact with the first electrode and the second electrode.

14. The method of claim 8, further comprising obtaining a hydration level measurement based on the signals received from the first electrode and the second electrode.

15. A non-transitory computer-readable medium comprising processor-executable instructions configured to cause a processor to:
receive a user input to place a wearable device into a measurement mode, the wearable device comprising a multifunction contact button coupled to an outer body of the wearable device, the outer body shaped as a part of a wristwatch and configured to be wearable by a user on the user's wrist adjacent to a first hand of the user, the wearable device further comprising a plurality of sensors physically coupled to the outer body, a first sensor of the plurality of sensors comprising a first electrode coupled to the outer body, the first electrode positioned to be contacted by the user's wrist, and the multifunction contact button comprising a second electrode of the first sensor, the multifunction contact button positioned to be contacted by a finger or thumb of a second hand of the user, the multifunction contact button capable of (i) receiving user input to interact with the wearable device, (ii) transitioning the wearable device from a normal course of operation to a measurement mode and initiating an electrocardiogram ("ECG") measurement, and (iii) transitioning the wearable device from the normal course of operation to a measurement mode and initiating a photoplethysmography ("PPG") measurement using a second sensor of the plurality of sensors, and is configured to, based on a contact, perform (i), (ii), (iii), or a combination thereof, wherein the measurement mode is activated based on a user interaction indicating a desire to obtain a bodily function measurement, and wherein the normal course of operation allows background ECG or PPG measurements;
receive, in the measurement mode, signals from the first electrode and the second electrode;
receive, in the measurement mode, signals from a second sensor of the plurality of sensors;
obtain, in the measurement mode, an electrocardiography ("ECG") measurement based on the signals received from the first electrode and the second electrode; and
obtain, in the measurement mode, a photoplethysmography (PPG) measurement using the second sensor.

16. The non-transitory computer-readable medium of claim 15, further comprising processor-executable instructions configured to cause the processor to:
measure electrical impulses received by the first electrode and the second electrode; and
determine the ECG measurement based on the measured electrical impulses.

17. The non-transitory computer-readable medium of claim 15, further comprising processor-executable instructions configured to cause the processor to receive further user input, via the multifunction contact button, to an application on the wearable device.

18. The non-transitory computer-readable medium of claim 15, wherein the user input to interact with the wearable device comprises non-sensor related activities.

19. The non-transitory computer-readable medium of claim 15, further comprising processor-executable instructions configured to cause the processor to obtain the ECG measurement in response to the user in contact with the second electrode and the first electrode.

20. The non-transitory computer-readable medium of claim 15, further comprising processor-executable instructions configured to cause the processor to obtain a hydration level measurement based on the signals received from the first electrode and the second electrode.

* * * * *